US011969724B2

(12) United States Patent
Liang et al.

(10) Patent No.: US 11,969,724 B2
(45) Date of Patent: Apr. 30, 2024

(54) OCM REACTOR SYSTEM CONTAINING A MULTI COMPONENT CATALYST SYSTEM

(71) Applicant: SABIC Global Technologies B.V., Bergen op Zoom (NL)

(72) Inventors: Wugeng Liang, Bengaluru (IN); Hector Perez, Bengaluru (IN); Pankaj Gautam Singh, Bengaluru (IN); David West, Bengaluru (IN)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 18/038,547

(22) PCT Filed: Dec. 7, 2021

(86) PCT No.: PCT/EP2021/084539
§ 371 (c)(1),
(2) Date: May 24, 2023

(87) PCT Pub. No.: WO2022/122712
PCT Pub. Date: Jun. 16, 2022

(65) Prior Publication Data
US 2023/0347309 A1   Nov. 2, 2023

(30) Foreign Application Priority Data
Dec. 8, 2020  (EP) ..................... 20212400

(51) Int. Cl.
*B01J 8/04*      (2006.01)
*B01J 21/04*     (2006.01)
(Continued)

(52) U.S. Cl.
CPC .......... *B01J 8/0438* (2013.01); *B01J 8/0492* (2013.01); *B01J 21/04* (2013.01); *B01J 23/63* (2013.01);
(Continued)

(58) Field of Classification Search
CPC ......... B01J 8/00; B01J 8/02; B01J 8/04; B01J 8/0403; B01J 8/0423; B01J 8/0438;
(Continued)

(56) References Cited

FOREIGN PATENT DOCUMENTS

| WO | 2016094476 A1  | 6/2016 |
| WO | 20180175535 A1 | 9/2018 |
| WO | 20220122712 A1 | 6/2022 |

OTHER PUBLICATIONS

Foreign Communication from Related Application—International Search Report and Written Opinion of the International Searching Authority, International Application No. PCT/EP2021/084539, dated Feb. 18, 2022, 8 pages.

*Primary Examiner* — Natasha E Young
(74) *Attorney, Agent, or Firm* — Conley Rose, P.C.; Rodney B. Carroll (57) ABSTRACT

The invention relates to a reactor system for oxidative coupling of methane (OCM), comprising: reactor system for oxidative coupling of methane (OCM), comprising: (a) an inlet configured to receive a reactant mixture; (b) a reaction chamber having an upstream end and a downstream end such that the reaction chamber extends from the upstream end to the downstream end, and the reaction chamber comprises a catalyst bed having a catalyst composition having at least two catalyst components: (i) a low selectivity catalyst component; and (ii) a high selectivity catalyst component; and (c) an outlet configured to recover a $C_{2+}$ hydrocarbon product mixture from the reactor system; wherein the reactor system is configured such that the reactant mixture substantially contacts the high selectivity catalyst component prior to contacting the low selectivity catalyst component. The invention further describes a process for the production of $C_{2+}$ hydrocarbon product mixture using the present reactor system.

20 Claims, 3 Drawing Sheets

(51) Int. Cl.
*B01J 23/63* (2006.01)
*C07C 2/84* (2006.01)

(52) U.S. Cl.
CPC ............ *C07C 2/84* (2013.01); *C07C 2521/04* (2013.01); *C07C 2523/63* (2013.01)

(58) Field of Classification Search
CPC . B01J 8/0492; B01J 21/00; B01J 21/02; B01J 21/04; B01J 23/00; B01J 23/38; B01J 23/54; B01J 23/56; B01J 23/63; C07C 2/00; C07C 2/76; C07C 2/82; C07C 2/84; C07C 2521/00; C07C 2521/02; C07C 2521/04; C07C 2523/00; C07C 2523/38; C07C 2523/54; C07C 2523/56; C07C 2523/63; C07C 2523/06
See application file for complete search history.

OCM REACTOR SYSTEM CONTAINING A MULTI COMPONENT CATALYST SYSTEM

CROSS REFERENCE TO RELATED APPLICATIONS

This application is a filing under 35 U.S.C. 371 of International Application No. PCT/EP2021/084539 filed Dec. 7, 2021, entitled "An OCM Reactor System Containing a Multi Component Catalyst System," which claims priority to Europe Patent Application No. 20212400.4 filed Dec. 8, 2020, which applications are incorporated by reference herein in their entirety.

FIELD OF INVENTION

The invention relates to the field of reactor systems configured with catalyst systems suitable for the oxidative coupling of methane (OCM).

BACKGROUND

Methane is a widely available feedstock and if oxidatively coupled in presence of oxygen using suitable reactor systems, commercially high value chemicals, such as ethylene and other $C_{2+}$ hydrocarbons, can be produced at high production margins. However, one of the reasons why OCM process has not been used extensively under commercial operations is because traditional OCM catalyst systems suffer from low product selectivity towards ethylene and other $C_{2+}$ hydrocarbons. Product selectivity, in particular is a concern for any OCM process, where often the OCM process results in the formation of waste byproducts (e.g. $CO_2$) instead of the intended $C_{2+}$ hydrocarbons, resulting in operational inefficiency and increased operational expenditure (OpEx). Typically in OCM reactions, as the feed mixture primarily contains methane, relatively an inert hydrocarbon, the feed introduced in the reactor is often pre-heated to high temperature to activate the methane for OCM reactions. Such heating steps may be carried out using heat exchangers, which are expensive and renders the OCM process both capital and operationally expensive. Therefore, for OCM reactions, if the catalyst bed is able to be ignited at relatively low temperature to carry out the OCM reaction, the requirement of heat exchangers to preheat the feed is omitted. In other words, it is desirable for a catalyst system to have a low ignition temperature. Several attempts were tried in the past on selection of different catalyst system such as single, double or multiple catalyst systems for oxidative coupling of methane. Particularly, WO2016094476A1 discloses "A method of producing ethylene from a reactant mixture comprising methane (CH4) and oxygen (O2), the method comprising: contacting the reactant mixture with a catalytic material to produce a product stream comprising ethylene, wherein the ethylene is obtained from oxidative coupling of CH4, wherein heat produced by the oxidative coupling of CH4 is transferred to an inert material in an amount sufficient to reduce thermal deactivation of the catalytic material".

Figure 3:
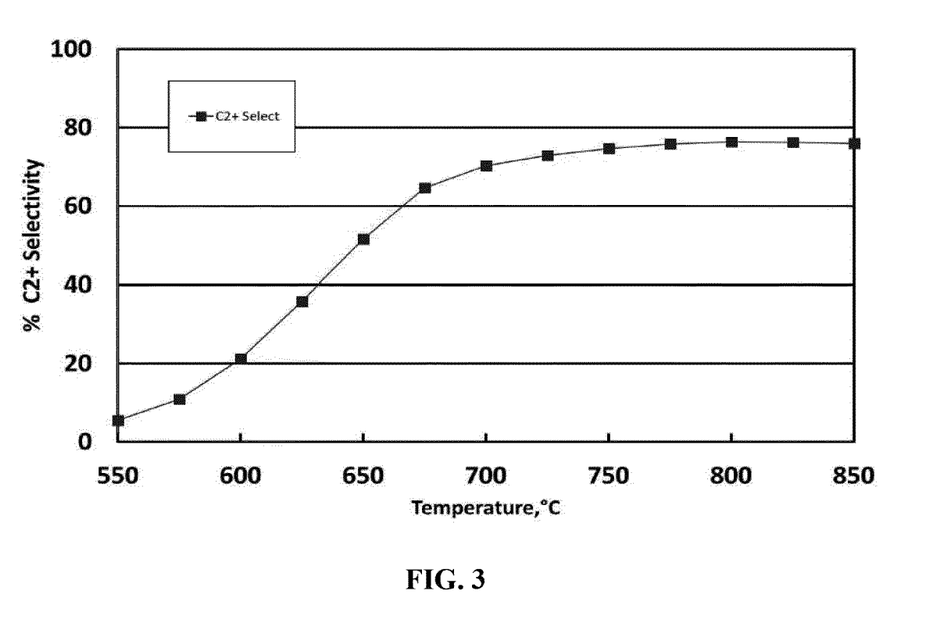
FIG. 3 is a graphical representation of $C_{2+}$ hydrocarbon selectivity obtained for the Comparative Example 1 (CE1) catalyst system at different catalyst bed temperature.

Thus a key consideration for an OCM process is the ignition temperature at which an OCM catalyst enables the conversion of at least 90% of the oxygen present in a methane-containing feed to produce $C_{2+}$ hydrocarbon products. Certain OCM catalyst systems have high ignition temperature, which translates to requiring high catalyst bed temperature to carry out the OCM reaction. However, under such conditions, there is a possibility that the catalyst may itself degrade on prolonged exposure to high temperature or in certain instance the $C_{2+}$ hydrocarbon product once formed, may undergo further conversion to oxide byproducts ($CO_2$). On the other hand, under conditions of low catalyst bed temperature, the catalyst does not get sufficiently ignited affecting both selectivity and activity performance of the catalyst. Further, as shown in this disclosure under FIG. 3, OCM catalysts in general have poor selectivity under low temperature conditions. It is therefore desired by industry practitioners, to conduct OCM reactions at low catalyst bed temperature yet sufficient to ignite the catalyst without adversely affecting its selectivity performance.

In particular, the interplay between catalyst bed temperature, ignition temperature and catalyst selectivity becomes an important consideration for an OCM process due to a temperature gradient (non-uniform temperature distribution) that typically develops across a catalyst bed, which affects OCM reaction. Such a temperature gradient, creates pockets of temperature zones across the entire catalyst bed, which can affect the overall catalyst and process performance. For example, if a high ignition temperature OCM catalyst is used in a relatively low temperature zone, the catalyst will not be sufficiently ignited and will affect the overall catalyst performance. The non-uniform temperature across a catalyst bed becomes more pronounced when the reactor dimensions are large especially in a commercial set up, where there are large domains of uneven temperature zones, which in turn severely affects selectivity performance of the catalyst.

Therefore, for the foregoing reasons, there remains a need to develop an improved catalytic reactor system with better heat management for carrying out OCM reactions at high product selectivity while ensuring that the catalyst system is configured in a manner to be ignited at a sufficiently low temperature.

SUMMARY

A solution to some or all of the drawbacks and limitations described above, resides in the present inventive reactor configuration. Accordingly, the present invention relates to a reactor system for oxidative coupling of methane (OCM), comprising: (a) an inlet configured to receive a reactant mixture; (b) a reaction chamber having an upstream end and a downstream end such that the reaction chamber extends from the upstream end to the downstream end, wherein the reaction chamber comprises a catalyst bed having a catalyst composition having at least two catalyst components: (i) a low selectivity catalyst component; and (ii) a high selectivity catalyst component; and (c) an outlet configured to recover a $C_{2+}$ hydrocarbon product mixture from the reactor system; wherein the reactor system is configured such that the reactant mixture substantially contacts the high selectivity catalyst component prior to contacting the low selectivity catalyst component. The expression "the reactant mixture substantially contacts the high selectivity catalyst component prior to contacting the low selectivity catalyst component" means that all or nearly all of the reactant mixture first contacts the high selectivity catalyst component before coming in contact with the low selectivity catalyst component. In some embodiments of the invention the expression "the reactant mixture substantially contacts the high selectivity catalyst component prior to contacting the low selectivity catalyst component" means that at least 98%, preferably at least 99%, or most preferably 100% of the reactant mixture contacts the high selectivity catalyst component prior to the reactant mixture contacting the low selectivity catalyst component.

In some embodiments of the invention, the catalyst bed comprises the low selectivity catalyst component present in an amount greater than 10 wt. %, with regard to the total weight of the catalyst composition. In some embodiments of the invention, the high selectivity catalyst component is positioned proximal to the inlet and the low selectivity catalyst component is positioned proximal to the outlet. In some embodiments of the invention, the high selectivity catalyst component is positioned at the upstream end of the reactor chamber and the low selectivity catalyst component is positioned at the downstream end of the reactor chamber. In some embodiments of the invention, the catalyst bed comprises the high selectivity catalyst component present in an amount of at least 50 wt. % to less than 90 wt. % with regard to the total weight of the catalyst composition. In some preferred embodiments of the invention, the high selectivity catalyst component and the low selectivity catalyst component are in contact with each other.

In some embodiments of the invention, the catalyst bed comprises the low selectivity catalyst component present in an amount greater than 10 wt. % to less than 50 wt. % with regard to the total weight of the catalyst composition. In some embodiments of the invention, the ratio of $C_{2+}$ hydrocarbon product selectivity of the high selectivity catalyst component to the $C_{2+}$ hydrocarbon product selectivity of the low selectivity catalyst component is greater than 1.5.

In some embodiments of the invention, the low selectivity catalyst component is characterized by an ignition temperature of at least 100° C. lower than the ignition temperature of the high selectivity catalyst component, when each of the low selectivity catalyst component and the high selectivity catalyst component is subjected to a reaction condition sufficient to produce $C_{2+}$ hydrocarbon mixture product. In some embodiments of the invention, the catalyst composition is characterized by a $C_{2+}$ hydrocarbon product selectivity of greater than 70% with regard to the total product formed and an ignition temperature of less than 700° C. when the catalyst composition is subjected to a reaction condition sufficient to produce $C_{2+}$ hydrocarbon mixture product. In some preferred embodiments of the invention, the catalyst composition is characterized by a $C_{2+}$ hydrocarbon product selectivity of greater than 70% with regard to the total product formed and an ignition temperature of less than 700° C. when the catalyst composition is subjected to a reaction condition sufficient to produce $C_{2+}$ hydrocarbon mixture product, and/or wherein the ratio of $C_{2+}$ hydrocarbon product selectivity of the high selectivity catalyst component to the $C_{2+}$ hydrocarbon product selectivity of the low selectivity catalyst component is greater than 1.5.

In some embodiments of the invention, (a) the high selectivity catalyst component is represented by a general formula (I): $(AE_aRE1_bRE2_cAT_dO_x)/M_mO_n$, and (b) the low selectivity catalyst component is represented by a general formula (II): $(AM)_z(AE_aRE1_bRE2_cAT_dO_x)/M_mO_n$; wherein, (i) 'AE' represents an alkaline earth metal; (ii) 'RE1' represents a first rare earth element; (iii) 'RE2' represents a second rare earth element; (iv) 'AT' represents a third rare earth element 'RE3', or a redox agent 'RX' selected from antimony, tin, nickel, chromium, molybdenum, tungsten, manganese, bismuth; wherein, 'a', 'b', 'c', and 'd' each independently represents relative molar ratio; wherein 'a' ranges from 0.1 to 5; 'b' ranges from 0.1 to 10; 'c' ranges from 0.01 to about 10; 'd' ranges from 0.01 to 10; 'x' balances the oxidation state; wherein, the first rare earth element, the second rare earth element and the third rare earth element, are different; (v) 'AM' represents a metal promoter selected from Group 4 to Group 12 of the Periodic Group of Elements; (vi) 'z' represents the amount of metal promoter present in the low selectivity catalyst component and 'z' ranges from 0.01 wt. % to 1.0 wt. % with regard to the weight of the low selectivity catalyst component; and (vii) '$M_mO_n$' represents an oxide catalyst support, wherein 'M' is selected from a metal or silicon; 'm' and 'n' are any positive integers and ranges from about 1 to about 5.

In some preferred embodiments of the invention, the metal promoter 'AM' is selected from the Group 10 metals of the Periodic Group of Elements. In some embodiments of the invention, the metal promoter 'AM' is palladium. In some embodiments of the invention, the metal promoter 'AM' is selected from the Group 10 metals of the Periodic Group of Elements, preferably wherein the metal promoter 'AM' is palladium.

In some embodiments of the invention, the metal promoter 'AM' is present in an amount 'z' ranging from 0.02 wt. % to 0.1 wt. %, with regard to the weight of the low selectivity catalyst component.

In some embodiments of the invention, the alkaline earth metal 'AE' is selected from the group consisting of magnesium, calcium, strontium, barium, and combinations thereof. In some preferred embodiments of the invention, the alkaline earth metal 'AE' is strontium. In some embodiments of the invention, the alkaline earth metal 'AE' is selected from the group consisting of magnesium, calcium, strontium, barium, and combinations thereof, preferably wherein the alkaline earth metal 'AE' is strontium. In some embodiments of the invention, the first rare earth element 'RE1', the second rare earth element 'RE2', and the third rare element 'RE3', are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In some embodiments of the invention, the metal 'M' of the oxide catalyst support $M_mO_n$ is selected from aluminum, zinc, tin (II), and lead (II). In some preferred embodiments of the invention, the oxide catalyst support ($M_mO_n$) is aluminum oxide ($Al_2O_3$). In some embodiments of the invention, metal 'M' of the oxide catalyst support $M_mO_n$ is selected from aluminum oxide ($Al_2O_3$), zinc oxide, tin (II) oxide, and lead (II) oxide, preferably the oxide catalyst support ($M_mO_n$) is aluminum oxide ($Al_2O_3$).

In some aspects of the invention, the present invention is directed to a process for producing a $C_{2+}$ hydrocarbon mixture product, comprising: (a) introducing the reactant mixture comprising methane and oxygen, into the reactor system of the present invention by means of the inlet; (b) substantially contacting the reactant mixture with the high selectivity catalyst component and thereafter substantially contacting the reactant mixture with the low selectivity catalyst component to form a precursor hydrocarbon mixture product; and (c) removing unconverted methane from the precursor hydrocarbon mixture product and thereafter recovering the $C_{2+}$ hydrocarbon mixture product by means of the outlet. In some aspects of the invention, the reactant mixture introduced at the inlet has a methane to oxygen molar ratio ranging from 2:1 to 15:1.

In some aspects of the invention, the invention is related to a catalyst bed having a catalyst composition suitable for the oxidative coupling of methane, wherein the catalyst composition comprises: (a) at least 50 wt. % to less than 90 wt. % with regard to the total weight of the catalyst composition, a high selectivity catalyst component represented by a general formula (I): $(AE_aRE1_bRE2_cAT_dO_x)/M_mO_n$, and (b) greater than 10 wt. % to less than 50 wt. % with regard to the total weight of the catalyst composition, a low selectivity catalyst component represented by a general formula (II): $(AM)_z\text{-}(AE_aRE1_bRE2_cAT_dO_x)/M_mO_n$; wherein, (i) 'AE' represents an alkaline earth metal; (ii) 'RE1' represents a first rare earth element; (iii) 'RE2' represents a second rare earth element; (iv) 'AT' represents a third rare earth element 'RE3', or a redox agent 'RX' selected from antimony, tin, nickel, chromium, molybdenum, tungsten, manganese, bismuth; wherein, 'a', 'b', 'c', and 'd' each independently represents relative molar ratio; wherein 'a' ranges from 0.1 to 5; 'b' ranges from 0.1 to 10; 'c' ranges from 0.01 to about 10; 'd' ranges from 0.01 to 10; 'x' balances the oxidation state; wherein, the first rare earth element, the second rare earth element and the third rare earth element, are different; (v) 'AM' represents a metal promoter selected from Group 4 to Group 12 of the Periodic Group of Elements; (vi) 'z' represents the amount of metal promoter present in the low selectivity catalyst component and 'z' ranges from 0.01 wt. % to 1.0 wt. % with regard to the weight of the low selectivity catalyst component; and (vii) '$M_mO_n$' represents an oxide catalyst support, wherein 'M' is selected from a metal or silicon; 'm' and 'n' are any positive integer and ranges from about 1 to about 5.

The expression "different" as used herein means that each of the rare earth elements are different chemical elements. Further, it is understood by those skilled in the art that where reference is made herein to balancing of the oxidation state with respect to the composition, the balancing is to achieve electro-neutrality of the overall composition containing the catalyst of the present invention.

Other objects, features and advantages of the invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from some specific embodiments may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION

The invention is based, in part, on the discovery that a rector system having a unique catalyst configuration can be used for OCM reaction to generate $C_{2+}$ hydrocarbon products at high selectivity while ensuring that the catalyst system is ignited at a sufficiently low temperature. Accordingly, the invention as described in this disclosure provides for a reactor system comprising a catalyst bed containing a catalyst composition configured to conduct the OCM reaction at high selectivity towards $C_{2+}$ hydrocarbon products while ensuring that the catalyst bed is ignited at low ignition temperature. In particular, the reactor system contains a catalyst bed comprising a catalyst composition having at least two catalyst components, each having distinct selectivity characteristic such that a particular catalyst component has a higher $C_{2+}$ hydrocarbon selectivity when compared to the other catalyst component constituting the catalyst composition. Further, the reactor system is configured in a manner that results in the OCM reactant feed stream substantially contacting the catalyst component having higher $C_{2+}$ hydrocarbon selectivity prior to contacting the catalyst component having lower $C_{2+}$ hydrocarbon selectivity. The inventors surprisingly found that only when a specific proportion of the low selectivity catalyst component is present in the catalyst bed, the desired balance of $C_{2+}$ hydrocarbon selectivity and ignition temperature is achieved. This understanding is also evidenced from the performance of the catalyst system under Comparative Example 5 (CE5) illustrated in this disclosure.

The following includes definitions of various terms, expressions and phrases used throughout this specification.

The expressions "about" or "approximately" are defined as being close to as understood by one of ordinary skill in the art. In some non-limiting embodiments the terms are defined to be within 1%, preferably, within 0.1%, more preferably, within 0.01%, and most preferably, within 0.001%. The expressions "wt. %", "vol. %", or "mol. %" refers to a weight, volume, or molar percentage of a component, respectively, based on the total weight, the total volume, or the total moles of material that includes the component. In a non-limiting example, 10 moles of a particular component present in a 100 moles of a material is 10 mol. % of component. The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The method of the invention can "comprise," "consist essentially of," or "consist of" particular ingredients, components, compositions, etc., disclosed throughout the specification. Any numerical range used through this disclosure shall include all values and ranges there between unless specified otherwise. For example, a boiling point range of 50° C. to 100° C. includes all temperatures and ranges between 50° C. and 100° C. including the temperature of 50° C. and 100° C.

The expression "$C_{2+}$ hydrocarbon" or "$C_{2+}$ hydrocarbon mixture product" as used in this disclosure means the hydrocarbon products having at least two carbon atoms including ethylene, ethane, ethyne, propene, propane, and $C_4\text{-}C_5$ hydrocarbons, which are produced using the inventive composition containing the catalyst of the present invention. The expression oxidative coupling of methane or "OCM" as referred or used throughout this disclosure means the oxidative coupling of methane or the reaction of methane and oxygen, for the production of $C_{2+}$ hydrocarbons from methane. The expression "redox agent" as used though out this disclosure means substances or elements, which are capable of undergoing or promoting either oxidation or reduction reactions.

The expression "selectivity" or "product selectivity" to a desired product or products refers to how much desired product was formed divided by the total products formed, both desired and undesired. For purposes of the disclosure herein, the selectivity to a desired product is a percentage selectivity based on moles converted into the desired product. Further, for purposes of the disclosure herein, a $C_x$ selectivity (e.g., $C_2$ selectivity, $C_{2+}$ selectivity, etc.) can be calculated by dividing a number of moles of carbon (C) from $CH_4$ that were converted into the desired product (e.g., $C_{C2H4}$, $C_{C2H6}$, etc.) by the total number of moles of C from $CH_4$ that were converted (e.g., $C_{C2H4}$, $C_{C2H6}$, $C_{C2H2}$, $C_{C3H6}$, $C_{C3H8}$, $C_{C4s}$, $C_{CO2}$, $C_{CO}$, etc.). $C_{C2H4}$=number of moles of C from $CH_4$ that were converted into $C_2H_4$; $C_{C2H6}$=number of moles of C from $CH_4$ that were converted into $C_2H_6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4s}$=number of moles of C from $CH_4$ that were converted into $C_4$ hydrocarbons ($C_4$s); $C_{CO2}$=number of moles of C from $CH_4$ that were converted into $CO_2$; $C_{CO}$=number of moles of C from $CH_4$ that were converted into CO; etc. Specifically, $C_{2+}$ hydrocarbon selectivity (e.g., selectivity to $C_{2+}$ hydrocarbons) refers to how much $C_2H_4$, $C_3H_6$, $C_2H_2$, $C_2H_6$, $C_3H_8$, $C_5$s and $C_4$s were formed divided by the total product formed which includes $C_2H_4$, $C_3H_6$, $C_2H_2$, $C_2H_6$, $C_3H_8$, $C_4$s, $C_5$s, $C_{n's}$ $CO_2$ and CO. Accordingly, a preferred way of calculating $C_{2+}$ hydrocarbon selectivity will be by using the equation (Eqn 1):

$$\left\{ \frac{\begin{array}{c}(2C_{C2H4} + 2C_{C2H6} + 2C_{C2H2} + \\ 2C_{C3H6} + 3C_{C3H8} + 4C_{C4s} + 5C_{C5s} + nC_{Cn's})\end{array}}{\begin{array}{c}(2C_{C2H4} + 2C_{C2H6} + 2C_{C2H2} + 2C_{C3H6} + 3C_{C3H8} + \\ 4C_{C4s} + 5C_{C5s} + nC_{Cn's} + C_{CO2} + C_{CO})\end{array}} \right\} \times 100$$

Specifically, a high $C_{2+}$ hydrocarbon selectivity will signify increased formation of useful $C_{2+}$ hydrocarbon products over that of undesirable carbon oxide byproducts. The term "total product formed" used in the context of measuring selectivity includes $C_2H_4$, $C_3H_6$, $C_2H_2$, $C_2H_6$, $C_3H_8$, $C_4$s, $C_5$s, $C_{n's}$ $CO_2$ and CO.

The expression "carbon efficiency (CE)" as used in this disclosure is defined as the efficiency with which one mole of methane is selectively converted to specific $C_{2+}$ hydrocarbon products with the assumption that part of the carbon monoxide and hydrogen generated during the OCM reaction is recycled back and converted to methane feed. The carbon efficiency is calculated using Eqn 2 shown below where the expression "S" stands for selectivity. For example "$S_{ethylene}$" stands for selectivity of ethylene:

$$(CE = S_{ethylene}\% + S_{propylene}\% + 0.9 \times S_{ethane}\% + 0.7 \times S_{propane}\% + 0.7 \times S_{co}\% + 0.25\% \ S_{(C4-C5)}) \qquad \text{-Eqn 2}$$

The expression "high selectivity catalyst component" means a catalyst component having $C_{2+}$ hydrocarbon selectivity higher than the low selectivity catalyst component. The expression "low selectivity catalyst component" means a catalyst component having $C_{2+}$ hydrocarbon selectivity lower than the high selectivity catalyst component. In other words, the "low selectivity catalyst component" has selectivity relatively lower than the "high selectivity catalyst component" although in absolute terms the selectivity of the "low selectivity catalyst component" may still be higher than many existing OCM catalyst system.

The expression "ignition temperature" as used in this disclosure means the average catalyst bed temperature at which at least 90% of the oxygen present in the feed/reactant mixture is converted to $C_{2+}$ hydrocarbon product mixture. In general, the low selectivity catalyst component has low ignition temperature and the high selectivity catalyst component has high ignition temperature. The expression "the reactant mixture substantially contacts the high selectivity catalyst component prior to contacting the low selectivity catalyst component" as used throughout this disclosure, means that at least 98%, preferably at least 99%, or most preferably 100% of the reactant mixture contacts the high selectivity catalyst component prior to the reactant mixture contacting the low selectivity catalyst component.

The expression "upstream end" with respect to the reactor system means the section of the reactor chamber in which the feed/reactant mixture is introduced in the reaction chamber. The expression "downstream end" with respect to the reactor system means the section of the reactor chamber from where the product formed after the OCM reaction, is recovered after the reactant mixture flowing from the upstream end contacts both the catalyst components.

Figure 1:
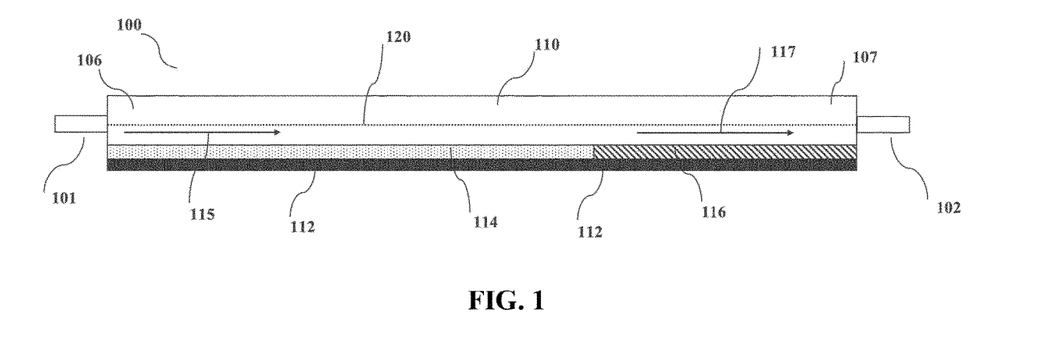
FIG. 1 is an illustration of a reactor system as an embodiment of the invention.

Referring to FIG. 1, in some embodiments of the invention, the present invention relates to a reactor system (100) for oxidative coupling of methane (OCM), comprising: (a) an inlet (101) configured to receive a reactant mixture (115); (b) a reaction chamber (110) having an upstream end (106) and a downstream end (107) such that the reaction chamber (110) extends from the upstream end (106) to the downstream end (107), wherein the reaction chamber (110) comprises a catalyst bed (112) having a catalyst composition having at least two catalyst components: (i) a low selectivity catalyst component (116); and (ii) a high selectivity catalyst component (114); and (c) an outlet (102) configured to recover a $C_2$ hydrocarbon product mixture from the reactor system (100); wherein the reactor system (100) is configured such that the reactant mixture (115) substantially contacts the high selectivity catalyst (114) component prior to contacting the low selectivity catalyst component (116). In some aspects of the invention, the reactor system (100) has a principal axis (120) coaxial to the inlet (101) and the outlet (102). As may be appreciated by a skilled person, in some embodiments of the invention, the upstream end (106) and the downstream end (107) of the reactor system (100) are always in fluid communication with each other such that the reactant mixture (115) passes from the upstream end (106) of the reactor system (100) to the downstream end (107) of the reactor system (100). In some aspects of the invention, the reactant mixture (115) has a relatively higher oxygen concentration than the reactant mixture (117).

In some embodiments of the invention, the catalyst bed (112) is a fixed bed catalyst. In some preferred aspects of the invention, low selectivity catalyst component (116) and the high selectivity catalyst component (114) are in contact with each other. Without wishing to be bound by any specific theory it is believed that the two catalyst components on being in contact with each other ensures suitable heat transfer and efficient management of the catalyst bed temperature.

In some embodiments of the invention, the high selectivity catalyst component (114) is positioned proximal to the inlet (101) and the low selectivity catalyst component (116)

is positioned proximal to the outlet (102). In some preferred embodiments of the invention, the high selectivity catalyst component (114) is positioned at the upstream end (106) of the reactor chamber (110) and the low selectivity catalyst component (116) is positioned at the downstream end (107) of the reactor chamber (110).

In some embodiments of the invention, the catalyst bed (112) comprises the low selectivity catalyst component (116) present in an amount greater than 10 wt. %, alternatively greater than 12 wt. %, or alternatively greater than 14 wt. %, with regard to the total weight of the catalyst composition. The inventors surprisingly found that when the low selectivity catalyst component (116) was present in an amount of 10 wt. % or less the desired balance of selectivity and ignition temperature was lost. This conclusion is also evidenced from the results of Comparative Example 5 (CE5) provided in this disclosure. In some embodiments of the invention, the catalyst bed (112) comprises low selectivity catalyst component (116) present in an amount of greater than 10 wt. % to less than 50 wt. %, alternatively at least 15 wt. % to less than 45 wt. %, alternatively from 25 wt. % to less than 40 wt. %, with regard to the total weight of the catalyst composition. In some embodiments of the invention, the catalyst bed (112) comprises the high selectivity catalyst component (114) present in an amount of at least 50 wt. % to less than 90 wt. %, alternatively at least 55 wt. % to less than 85 wt. %, alternatively at least 60 wt. % to less than 75 wt. %, with regard to the total weight of the catalyst composition.

In some embodiments of the invention, the ratio of $C_{2+}$ hydrocarbon product selectivity of the high selectivity catalyst component (114) to the $C_{2+}$ hydrocarbon product selectivity of the low selectivity catalyst component (116) is greater than 1.5, alternatively greater than 2, or alternatively greater than 2.5. In some embodiments of the invention, the low selectivity catalyst component (116) is characterized by an ignition temperature of at least 100° C., alternatively at least 120° C., alternatively at least 150° C., lower than the ignition temperature of the high selectivity catalyst component (114), when each of the low selectivity catalyst component (116) and the high selectivity catalyst component (114) is subjected to a reaction condition sufficient to produce $C_{2+}$ hydrocarbon mixture product. In some embodiments of the invention, the catalyst composition is characterized by a $C_{2+}$ hydrocarbon product selectivity of greater than 70%, alternatively greater than 71%, alternatively greater than 72%, alternatively greater than 75% with regard to the total product formed.

In some embodiments of the invention the catalyst composition is characterized by an ignition temperature of less than 700° C., alternatively less than 650° C., alternatively less than 600° C., alternatively less than 580° C. when the catalyst composition is subjected to a reaction condition sufficient to produce $C_{2+}$ hydrocarbon mixture product. The expression "total product formed" used in the context of measuring product selectivity includes the products formed such as $C_2H_4$, $C_3H_6$, $C_2H_2$, $C_2H_6$, $C_3H_8$, $C_4$s, $C_5$s, Cn's, $CO_2$ and CO.

Without wishing to be bound by any specific theory, it is believed that the unique arrangement of the high selectivity catalyst component (114) and the low selectivity catalyst component (116) is present in suitable amounts in the catalyst bed (112), which imparts a balance of selectivity and catalyst bed temperature to ignite the catalyst composition. Further, it is believed that the formation of carbon oxide byproducts is minimized by ensuring the reactant mixture (115) contacts the high selectivity catalyst component (114) at the upstream end (106) of the reaction chamber (110) prior to the reactant mixture (117) contacts the low selectivity catalyst component (116).

On the other hand, the present inventors found that when the low selectivity catalyst component (116) is placed at the upstream end (106) of the reactor chamber (110), carbon dioxide and carbon monoxide byproducts are formed at elevated and undesirable levels instead of ethylene and other desired hydrocarbons leading to reduced carbon efficiency. Further, as the downstream end of the reactor chamber (110) has relatively higher temperature due to heat generated from the progress of the exothermic OCM reaction, the heat so generated, flows from the downstream end (107) to the upstream end (106) (opposite to the flow of the feed or reactant mixture) until an equilibrium catalyst bed temperature is achieved throughout the catalyst bed (112). It is suspected that this possible mechanism ensures the removal of isolated temperature pockets in the reactor chamber and ensures the desired catalyst performance.

In some embodiments of the invention, (a) the high selectivity catalyst component (114) is represented by a general formula (I): $(AE_aRE1_bRE2_cAT_dO_x)/M_mO_n$, and the (b) low selectivity catalyst component (116) is represented by a general formula (II): $(AM)_z\text{-}(AE_aRE1_bRE2_cAT_dO_x)/M_mO_n$; wherein, (i) 'AE' represents an alkaline earth metal; (ii) 'RE1' represents a first rare earth element; (iii) 'RE2' represents a second rare earth element; (iv) 'AT' represents a third rare earth element 'RE3', or a redox agent 'RX' selected from antimony, tin, nickel, chromium, molybdenum, tungsten, manganese, bismuth; wherein, 'a', 'b', 'c', and 'd' each independently represent relative molar ratio; wherein 'a' ranges from 0.1 to 5, alternatively from about 0.2 to about 1, or alternatively from about 0.1 to about 0.6; 'b' ranges from 0.1 to 10, alternatively from about 0.5 to about 5, alternatively about 0.5 to about 1; 'c' ranges from 0.01 to about 10, alternatively from about 0.1 to 1, alternatively from about 0.1 to about 0.8; 'd' ranges from 0.01 to 10, alternatively from about greater than 0.1 to about 1, alternatively from about greater than 0.1 to about 0.4; 'x' balances the oxidation state; wherein, the first rare earth element, the second rare earth element and the third rare earth element, are different; (v) 'AM' represents a metal promoter selected from Group 4 to Group 12 of the Periodic Group of Elements; (vi) 'z' represents the amount of metal promoter present in the low selectivity catalyst component and 'z' ranges from 0.01 wt. % to 1.0 wt. % with regard to the weight of the low selectivity catalyst component; and (vii) '$M_mO_n$' represents an oxide catalyst support, wherein 'M' is selected from a metal or silicon; 'm' and 'n' are any positive integers and ranges from about 1 to about 5. The expression "different" as used herein means that each of the rare earth elements are different chemical elements. Further, it is understood by those skilled in the art that where reference is made herein to balancing of the oxidation state with respect to the composition, the balancing is to achieve electro-neutrality of the overall composition containing the catalyst of the present invention.

In some preferred embodiments of the invention, the metal promoter 'AM' is selected from the Group 10 metals of the Periodic Group of Elements. In some preferred embodiments of the invention, the metal promoter 'AM' is palladium. In some embodiments of the invention, the metal promoter 'AM' is present in an amount 'z' ranging from 0.01 wt. % to 0.1 wt. %, alternatively from 0.02 wt. % to 0.08 wt. %, with regard to the weight of the low selectivity catalyst component.

In some embodiments of the invention, the alkaline earth metal 'AE' is selected from the group consisting of magnesium, calcium, strontium, barium, and combinations thereof. In some preferred embodiments of the invention, the alkaline earth metal 'AE' is strontium. In some embodiments of the invention, the first rare earth element 'RE1', the second rare earth element 'RE2', and the third rare earth element 'RE3', are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In some embodiments of the invention, the metal 'M' of the oxide catalyst support $M_mO_n$ is selected from aluminum, zinc, tin (II), and lead (II). In some preferred embodiments of the invention, the oxide catalyst support ($M_mO_n$) is aluminum oxide (alumina) ($Al_2O_3$). Without wishing to be bound by any specific theory, the use of the oxide catalyst support provides mechanical stability to the overall catalyst system under extreme OCM reactor severities.

In some embodiments of the invention, the high selectivity catalyst component (114) can be prepared by a method comprising the steps of:
  a. providing an oxide catalyst support having the formula ($M_mO_n$) wherein 'M' is silicon or a metal selected from aluminum, zinc, tin (II), silicon, and lead (II); and 'm', and 'n' are any positive number and ranges from about 1 to about 5;
  b. providing an aqueous solution of a mixed metal oxide precursor comprising at least one compound containing an alkaline earth metal 'AE', at least one compound containing a first rare earth element 'RE1', at least one compound containing a second rare earth element 'RE2' and at least one compound containing a third rare earth element 'RE3' or a redox agent 'RX';
  c. impregnating the oxide catalyst support ($M_mO_n$) with the aqueous solution of the mixed metal oxide precursor and forming a supported catalyst precursor; and
  d. calcining the supported catalyst precursor at a temperature of at least 850° C., preferably for at least 900° C. and for at least 5 hours, or alternatively for at least 6 hours, and forming the catalyst composition.

The low selectivity catalyst component (116) may be prepared by contacting an aqueous solution comprising one or more compound containing the metal promoter (AM) with a portion of the high selectivity catalyst component and forming an impregnated catalyst precursor. Thereafter, the impregnated catalyst precursor is calcined at any temperature between 500° C.-900° C. to form the low selectivity catalyst component (116).

In some embodiments of the invention, at least one compound containing the first rare earth element 'RE1' is lanthanum nitrate. In some embodiments of the invention, at least one compound containing the alkaline earth metal 'AE' is strontium nitrate. In some embodiments of the invention, at least one compound containing the first rare earth element 'RE1' is lanthanum nitrate and at least one compound containing the alkaline earth metal 'AE' is strontium nitrate. In some embodiments of the invention, at least one compound containing the metal promoter (AM) is palladium nitrate.

In some embodiments of the invention, the aqueous solution of the mixed metal precursor can be prepared by dissolving in water at least one compound containing an alkaline earth metal 'AE', at least one compound containing a first rare earth element 'RE1', at least one compound containing a second rare earth element 'RE2', at least one compound containing a third rare earth element 'RE3'. In some preferred embodiments of the invention, the compound chosen is a nitrate salt for each of alkaline earth metal (AE), the first rare earth element (RE1), the second rare earth element (RE2), the third rare earth element (RE3) and the metal promoter (AM). In some embodiments of the invention, the mixed metal oxide precursor is obtained by dissolving the nitrate salts of alkaline earth metal (AE), first rare earth element (RE1), second rare earth element (RE2) in water. In some embodiments of the invention, the oxide catalyst support may be thermally treated prior to impregnating the support with the aqueous solution of the mixed metal oxide precursor in the oxide support.

In some aspects of the invention, the present invention is directed to a process for producing a $C_{2+}$ hydrocarbon mixture product, comprising: (a) introducing the reactant mixture (115) comprising methane and oxygen, into the reactor system (100) of the present invention, by means of the inlet (101); (b) substantially contacting the reactant mixture with the high selectivity catalyst component (114) and thereafter substantially contacting the reactant mixture (115) with the low selectivity catalyst component (116) to form a precursor hydrocarbon mixture product; and (c) removing unconverted methane from the precursor hydrocarbon mixture product and thereafter recovering the $C_{2+}$ hydrocarbon mixture product by means of the outlet (102).

In some aspects of the invention, the reactant mixture (115) introduced at the inlet (101) has a methane to oxygen molar ratio ranging from 2:1 to 15:1, alternatively from 4:1 to 10:1, alternatively from 5:1 to 8:1. In some embodiments of the invention, the reactant mixture (115) may be preheated to any temperature between 200° C. to 300° C. prior to introducing the reactant mixture (115) into the inlet (101). As may be appreciated by a skilled person, the reactant mixture (115) when it contacts the high selectivity catalyst component (114) has a relatively higher oxygen concentration as most of the oxygen is yet to be converted under the OCM reaction. On the other hand, the reactant mixture (117) when it contacts the low selectivity catalyst component (116) has a relatively low concentration of oxygen, as a portion of the initial amount of oxygen has already been converted under OCM conditions catalyzed by the high selectivity catalyst component (114). At this stage, of the reactant mixture (117) comprises unconverted methane, residual oxygen and products formed from the OCM reaction catalyzed by the high selectivity catalyst component (114).

The precursor hydrocarbon mixture product comprises $C_{2+}$ hydrocarbon product mixture generated from the OCM reaction catalyzed by each of the high selectivity catalyst component (114) and the low selectivity catalyst component (116) along with any residual unconverted methane. In some aspects of the invention, unconverted methane is removed from the $C_{2+}$ hydrocarbon mixture product. In some embodiments of the invention, the removal of unconverted methane from the $C_{2+}$ hydrocarbon mixture product is carried out using a distillation column. In some embodiments of the invention, the distillation column is a cryogenic distillation column. In some preferred embodiments of the invention, carbon monoxide (CO) and hydrogen produced during the OCM reaction is converted back to methane and re-introduced back to the feed/reactant mixture (115). In general as evident from the examples shown in this disclosure, $C_{2+}$ hydrocarbon selectivity and ignition temperature are opposite attributes (one increases as the other decreases and vice versa). However, the applicant unexpectedly found that in the present invention, the reactor system is configured with a catalyst composition in a manner such that the catalyst bed is ignited at a low ignition temperature while ensuring excellent product selectivity.

Methane coupling reaction under conditions suitable to produce $C_{2+}$ hydrocarbon mixture product include appropriate temperature conditions, pressure conditions, etc., to carry out the coupling reaction. In some embodiments of the invention, the reactor system (100) is a fixed bed reactor. In one preferred aspect of the invention, the reactor system is an adiabatic autothermal reactor having a fixed catalyst bed. In some aspects of the invention, the adiabatic autothermal reactor is a 2.3 mm ID quartz tube reactor.

In some embodiments of the invention, the pressure in the reactor is maintained at a pressure sufficient to carry out oxidative coupling of methane. The pressure may be maintained at a range of about 101.4 kN/m2 (14.7 psi) (ambient atmospheric pressure) to about 3447.5 kN/m$^2$ (500 psi), alternatively at a range of about 101.4 kN/m2 (14.7 psi) (ambient atmospheric pressure) to about 1379 kN/m$^2$ (200 psi), alternatively at a range of about 101.4 kN/m2 (14.7 psi) (ambient atmospheric pressure) to about 1034.2 kN/m$^2$ (150 psi). In some embodiments of the invention, the feed mixture is introduced into the reactor at a gas hourly space velocity (GHSV) ranging from about 500 h$^{-1}$ to about 1,000,000 h$^{-1}$, alternatively from about 1,000 h$^{-1}$ to about 500,000 h$^{-1}$, alternatively from about 5,000 h$^{-1}$ to about 400,000 h$^{-1}$.

Specific examples demonstrating some of the embodiments of the invention are included below. The examples are for illustrative purposes only and are not intended to limit the invention. It should be understood that the embodiments and the aspects disclosed herein are not mutually exclusive and such aspects and embodiments can be combined in any way. Those of ordinary skill in the art will readily recognize parameters that can be changed or modified to yield essentially the same results.

EXAMPLES

Comparative Example 1 (CE1)

Purpose: Comparative Example 1 (CE1) represents a high selectivity catalyst component and is represented by the general formula $Sr_{0.5}La_{1.8}Nd_{0.7}Yb_{0.1}/Al_2O_3$. The purpose of this example was to evaluate the performance of the high selectivity catalyst component where the catalyst bed is constituted with 100% by weight of the high selectivity catalyst component.

Materials: The following materials are procured and used for the synthesis of the compositions.

TABLE 1

| Comparative catalyst composition ($Sr_{0.5}La_{1.8}Nd_{0.7}Yb_{0.1}O_x/Al_2O_3$) | | | | |
|---|---|---|---|---|
| Catalyst composition: ($AE_aRE1_bRE2_cAT_dO_x$)/ $M_mO_n$ | Element/Compound used | Relative molar ratio | Precursor Material | Supplier |
| AE | Strontium (Sr) | a = 0.5 | Strontium Nitrate: $Sr(NO_3)_2$ | Sigma-Aldrich |
| RE1 | Lanthanum (La) | b = 1.8 | Lanthanum Nitrate $La(NO_3)_3 \cdot 6H_2O$ | Sigma-Aldrich |
| RE2 | Neodymium (Nd) | c = 0.7 | Neodymium Nitrate: $Nd(NO_3)_3 \cdot 6H_2O$ | Sigma-Aldrich |
| AT = RE3 | Ytterbium (Yb) | d = 0.1 | Ytterbium Nitrate $Yb(NO_3)_3 \cdot 5H_2O$ | Sigma-Aldrich |
| Alumina ($M_mO_n$) | Alumina ($Al_2O_3$) | | SA5162 Alumina | Saint-Gobain |

Catalyst preparation for CE1: The alumina support was crushed to 20-60 mesh and was dried at 120° C. overnight prior to use. 2.35 g of strontium nitrate ($Sr(NO_3)_2$), 0.50 g of ytterbium nitrate ($Yb(NO_3)_3 \cdot 6H_2O$), 8.64 g of lanthanum nitrate ($La(NO_3)_3 \cdot 6H_2O$), and 3.41 g of neodymium nitrate ($Nd(NO_3)_3 \cdot 6H_2O$) were dissolved in 10 mL of DI water to make a nitrate solution (may be referred to as aqueous solution of a mixed metal oxide precursor) of 0.5:0.1 1.8:0.7 molar ratio of Sr:Yb:La:Nd. After dissolving the nitrate compounds, the resultant nitrate solution (may be referred to as an aqueous solution of a mixed metal oxide precursor) was contacted with the alumina support until all of the nitrate solution is incorporated into the support (impregnation step). The material obtained was then dried at 120° C. and then calcined at 900° C. for 6 hours.

Catalyst evaluation and reactor configuration: The catalyst performance in terms of its selectivity and ignition temperature was evaluated using a 2.3 mm ID quartz tube reactor. For the performance evaluation of the catalyst, the catalyst composition obtained was sized to 40 to 60 mesh before loading into the reactor. The reactor was loaded with 20 mg of the catalyst. The reactant mixture comprised a mixture of methane and oxygen at a fixed methane to oxygen ($CH_4:O_2$) molar ratio of 7.4. The reactant mixture was fed to the reactor at a total flow rate of 40.0 sccm. The hydrocarbon products obtained were analyzed by using online GC with TCD and FID detectors. The temperature of the catalyst bed was measured using a thermocouple. The $C_{2+}$ hydrocarbon selectivity was measured using Eqn 1 and the carbon efficiency was measured using Eqn 2 after determining the products formed.

Results: The results from catalyst characterization and performance was evaluated in terms of carbon efficiency, ignition temperature, and $C_{2+}$ hydrocarbon product mixture. As shown under FIG. 3, when the catalyst bed temperature was maintained at 650° C., the selectivity was obtained at 51.6%; when the catalyst bed temperature was maintained at 600° C., the selectivity was obtained at only 21.2%, while at a temperature higher than 700° C., selectivity of 75% or higher was achieved. For a catalyst bed having non-uniform temperatures and having zones of temperature lower than 700° C., zones of temperature lower than 650° C. and zones of temperature lower than 600° C., the overall selectivity obtained will be the average of ~75%, ~ 50% and ~20% resulting in a reduced catalyst performance.

The $C_{2+}$ hydrocarbon selectivity of the Comparative Example 1 (CE1) catalyst system is reported at 77.5% and the ignition temperature was determined to be 700° C. The $C_{2+}$ hydrocarbon selectivity reported here is the maximum selectivity that was observed and the ignition temperature of 700° C. demonstrated the average catalyst bed temperature at which 90% of the oxygen present in the reactant mixture was converted to commercially useful hydrocarbon products. Therefore, although the CE1 catalyst system demonstrated excellent product selectivity, the ignition temperature required to carry out the OCM reaction was high. In other words, a reactor system using only CE1 catalyst system would require the reactant mixture to be preheated at relatively high temperature using capital intensive heat exchangers, in order to carry out the OCM reaction at high selectivity.

Comparative Example 2 (CE2)

Purpose: Comparative Example 2 (CE2) represents a low selectivity catalyst component and is represented by the general formula $Pd_{(0.025\%)}Sr_{0.5}La_{1.8}Nd_{0.7}Yb_{0.1}/Al_2O_3$. The formula for CE2 catalyst system is identical as that of the CE1 catalyst system except that a palladium based metal promoter was used. The purpose of this example was to evaluate the performance of the low selectivity catalyst component where the catalyst bed constituted 100% by weight of the low selectivity catalyst component.

Catalyst preparation: For preparing the CE2 catalyst system, 10% palladium nitrate solution was impregnated into 10.0 grams of CE1 catalyst system to form the catalyst system represented by the formula ($Pd_{(0.025\%)}Sr_{0.5}La_{1.8}Nd_{0.7}Yb_{0.1}/Al_2O_3$).

Results: The catalyst testing conditions and reactor configuration was kept identical as that practiced for Comparative Example 1 (CE1). The $C_{2+}$ hydrocarbon selectivity of the Comparative Example 2 (CE2) is reported at 38.9% and the ignition temperature was determined to be 550° C. The $C_{2+}$-hydrocarbon selectivity reported here is the maximum selectivity that was observed and the ignition temperature of 550° C. demonstrated the average catalyst bed temperature at which 90% of the oxygen present in the reactant mixture was converted to commercially useful products. Therefore, compared to the performance of the CE1 catalyst system, CE2 catalyst system demonstrates nearly half the selectivity performance but the catalyst itself gets ignited at a much reduced ignition temperature. Therefore, a reactor system using only CE2 catalyst system would result in poor selectivity performance. From the results obtained from CE1 catalyst system and CE2 catalyst system, it is apparent that $C_{2+}$ hydrocarbon selectivity and ignition temperature are opposite attributes i.e high selectivity comes at the cost of increased ignition temperature.

Inventive Example 1 (EX1)

Purpose: For Inventive Example 1 (EX1), the reactor system was configured such that the catalyst bed was loaded with 17 mg of the catalyst composition of Comparative Example 1 (CE1) which was placed proximal to the inlet at the upstream end of the reactor while 3 mg of the catalyst composition of Comparative Example 2 (CE2) was placed proximal to the outlet at the downstream end of the reactor. The total weight of the catalyst composition was maintained at 20 mg. Therefore, the catalyst system of EX1 contained a catalyst composition having 15 wt. % of the low selectivity catalyst component and 85 wt. % omgmgf the high selectivity catalyst component. The high selectivity catalyst component and the low selectivity catalyst component were kept in contact with each other.

Figure 2:
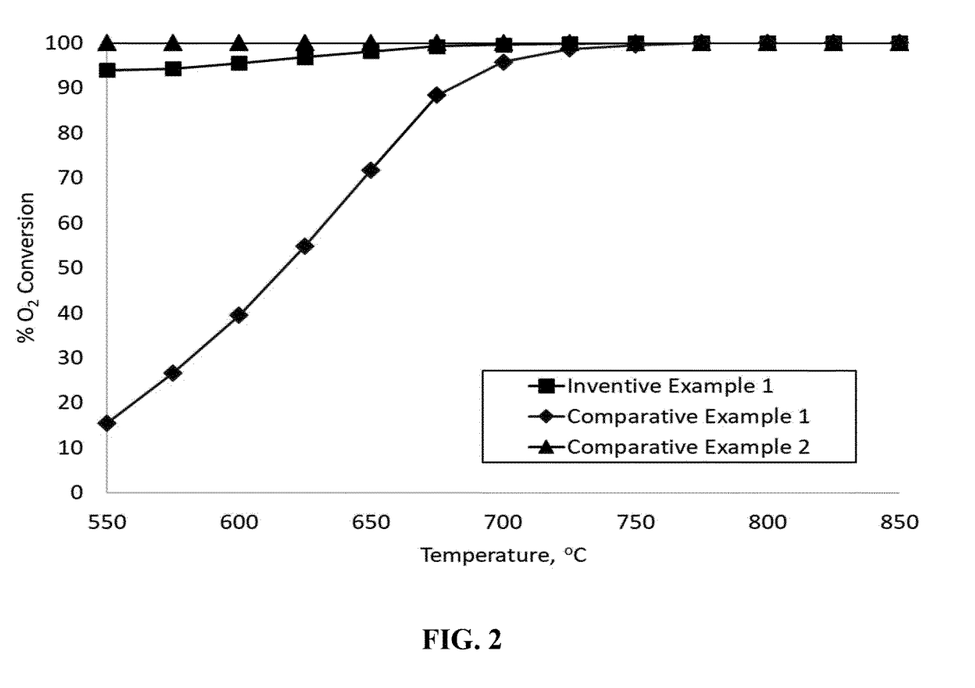
FIG. 2 is a graphical representation of the oxygen conversion at various catalyst bed temperature for the Inventive Example 1 (EX1) catalyst system, Comparative Example 1 (CE1) catalyst system and Comparative Example 2 (CE2) catalyst system.

Results: The process conditions used for carrying out the OCM reaction was identical to that described for the performance of the CE1 or CE2 catalyst systems. FIG. 2, provides an overview comparison of the oxygen conversion at various catalyst bed temperature for the Inventive Example 1 (EX1) catalyst system, Comparative Example 1 (CE1) catalyst system and Comparative Example 2 (CE2) catalyst system. It is evident from FIG. 2, that CE1 catalyst system is ignited at a relatively higher catalyst bed temperature at 700° C. (temperature at which oxygen conversion reaches 90% or higher) compared to the CE2 catalyst system and the inventive EX1 catalyst system.

The ignition temperature for EX1 catalyst system was obtained at 550° C., which indicates that at an average catalyst bed temperature of 550° C., at least 90% of the oxygen present in the reactant mixture was converted under OCM reaction conditions. On the other hand, the $C_{2+}$ hydrocarbon selectivity of the EX1 catalyst system is reported at 74.1% and represents the maximum selectivity obtained for the EX1 catalyst system. The inventors surprisingly found that the reactor system of EX1 was configured in a manner such that the ignition temperature was 150° C. lower than the CE1 catalyst system while ensuring that the $C_{2+}$ hydrocarbon selectivity is 90% higher than the CE2 catalyst system. For EX1 catalyst system, any low temperature zone due to the presence of CE1 catalyst system was offset by the heat generated from the reaction catalyzed by CE2 catalyst system at a much lower ignition temperature. As the overall reactor system operated at an ignition temperature as low as 550° C. the reactor system did not require additional heat exchanger systems to preheat the reactant mixture to carry out the OCM reaction. Further, it is evident that even at low temperature, the $C_{2+}$ hydrocarbon selectivity was not affected.

TABLE 2

Comparison between EX1, CE1 and CE2 performance results

| Example | Maximum $C_{2+}$ selectivity (%) | Ignition temperature (° C.) | Carbon efficiency (%) |
| --- | --- | --- | --- |
| EX1 | 74.1 | 550 | 74.3 |
| CE1 | 77.5 | 700 | 75.8 |
| CE2 | 38.9 | 550 | NA |

The above results demonstrates that the EX1 catalyst system can be used to eliminate the low temperature zones in the reactor chamber and ignite the catalyst bed at a relatively low temperature while retaining high selectivity. It is evident that the inventive reactor system of EX1, demonstrates a suitable balance of selectivity while achieving low ignition temperature.

Comparative Example 3 (CE3)

Purpose: The catalyst system of Comparative Example 3 (CE3) is similar to the catalyst system described under Comparative Example 2 (CE2) except that CE3 catalyst system has a higher metal promoter loading (0.05% in CE3 vs 0.025% in CE2). The CE3 catalyst system is represented by the formula $Pd_{(0.05\%)}Sr_{0.5}La_{1.8}Nd_{0.7}Yb_{0.1}/Al_2O_3$. The CE3 catalyst system may be regarded as a low selectivity catalyst component.

Result: The catalyst performance was evaluated under conditions similar to what was practiced for the catalyst system of CE1, CE2. The ignition temperature was obtained at 550° C. while the maximum selectivity for the $C_{2+}$ hydrocarbon was as low at 20.7%. Thus, CE3 catalyst systems with higher promoter metal content, the ignition temperature is reduced significantly compared to CE1 catalyst system. However, the reduction in ignition temperature comes at the cost of significantly reduced selectivity, which is unsustainable for commercial scale of OCM process.

Inventive Example 2 (EX2)

Purpose: For Inventive Example 2 (EX2) the reactor system was configured such that the catalyst bed was loaded with 17 mg of the catalyst composition of Comparative Example 1 (CE1) and was placed proximal to the inlet or the upstream end of the reactor system while 3 mg of the catalyst composition of Comparative Example 3 (CE3) was placed proximal to the outlet or the downstream end of the catalyst reactor. The total weight of the catalyst composition was maintained at 20 mg. Therefore, the catalyst system of EX3 contained a catalyst composition having 15 wt. % of the low selectivity catalyst component and 85 wt. % of the high selectivity catalyst component.

Result: The catalyst performance was evaluated under conditions identical to what was practiced for the catalyst systems described for CE1, CE2 and EX1. The ignition temperature was obtained at 550° C. while the selectivity for the $C_{2+}$ hydrocarbon was low at 72.5%. The table below (Table 3) provides a summary of the performance of the catalyst system for Inventive Example 2 (EX2) with the comparative catalyst systems of CE1 and CE3.

TABLE 3

Comparison between EX2, CE1 and CE3 performance results

| Example | Maximum $C_{2+}$ selectivity (%) | Ignition temperature (° C.) | Carbon efficiency (%) |
| --- | --- | --- | --- |
| EX. 2 | 72.5 | 550 | 73.2 |
| CE1 | 77.5 | 700 | 75.8 |
| CE3 | 20.7 | 550 | NA |

The reactor configuration containing the catalyst system EX2, demonstrated a suitable balance of selectivity as well ignition temperature. As is evident from Table 3, the inventive EX2 catalyst system demonstrates nearly 250% increase in selectivity compared to the CE3 catalyst system while having an ignition temperature about 150° C. lower than that obtained for CE1 catalyst system. Thus the reactor having the EX2 catalyst system demonstrates a synergistic balance of having the catalyst bed ignited at a low ignition temperature while retaining suitable selectivity.

Comparative Example 4 (CE4)

Purpose: The catalyst system of Comparative Example 4 (CE4) is similar to the catalyst system described under Comparative Example 2 (CE2) except that CE4 catalyst system was prepared by calcination at a lower temperature than the catalyst system of CE2 (500° C. for CE4 vs 900° C. for CE2). The CE4 catalyst system is represented by the general formula $(Pd_{(0.025\%)}Sr_{0.5}La_{1.8}Nd_{0.7}Yb_{0.1}/Al_2O_3)$.

Result: The catalyst performance was evaluated under conditions similar to what was practiced for the catalyst system of CE1, CE2, or CE3. The ignition temperature was obtained at 550° C. while the selectivity for the $C_{2+}$ hydrocarbon was low at 15.3%. As with CE3 catalyst system, CE4 catalyst system ignited at low ignition temperature but at the cost of reduced selectivity.

Inventive Example 3 (EX.3)

Purpose: For Inventive Example 3 (EX3) the reactor system was configured such that the catalyst bed was loaded with 17 mg of the catalyst composition of Comparative Example 1 (CE1) and placed proximal to the inlet at the upstream end of the reactor while 3 mg of the catalyst composition of Comparative Example 4 (CE4) was placed proximal to the outlet at the downstream end of the reactor. The total weight of the catalyst composition was maintained at 20 mg. Therefore, the catalyst system of EX3 contained a catalyst composition having 15 wt. % of the low selectivity catalyst component and 85 wt. % of the high selectivity catalyst component.

Result: The catalyst performance was evaluated under conditions identical to what was practiced for the catalyst systems described above such as CE1 catalyst system. The ignition temperature was obtained at 550° C. while the selectivity for the $C_{2+}$ hydrocarbon was low at 72.5%. The table below provides a summary of the performance of the catalyst system for Inventive Example 3 in comparison with the performance of the catalyst systems of CE1 and CE4.

TABLE 4

Comparison between EX. 3, CE1 and CE4 performance results

| Example | Maximum $C_{2+}$ selectivity (%) | Ignition temperature (° C.) | Carbon efficiency (%) |
| --- | --- | --- | --- |
| EX3 | 72.6 | 550 | 73.6 |
| CE1 | 77.5 | 700 | 75.8 |
| CE4 | 15.3 | 550 | NA |

From Table 4, the inventive EX3 catalyst system demonstrates nearly 350% increase in selectivity compared to the CE4 catalyst system while having an ignition temperature about 150° C. lower than that obtained for CE1 catalyst system. Thus the reactor system having the EX3 catalyst system, demonstrates a synergistic balance of low ignition temperature while retaining suitable selectivity.

Comparative Example 5 (CE5)

Purpose: The catalyst system of Comparative Example 5 (CE5) is similar to the catalyst system described under Inventive Example 1 (EX1) except that for the CE5 catalyst 5 system the catalyst bed contained 10 wt. % of the low selectivity catalyst composition instead of 15 wt. % of the low selectivity catalyst component.

Result: The catalyst performance was evaluated under conditions similar to what was practiced for the previous catalyst system of such as CE1 catalyst system. The ignition temperature was obtained at 700° C. while the selectivity for the $C_{2+}$ hydrocarbon was low at 77.2%. From the results obtained from the CE5 catalyst system, it is evident that in order to achieve a desired balance of suitable $C_{2+}$ hydrocarbon selectivity and low ignition temperature, the amount of low selectivity catalyst component present in the catalyst composition has to be greater than 10 wt. %. In other words, only when the reactor system is configured in a manner where the low selectivity catalyst component is purposefully present in an amount greater than 10 wt. %, that the intended performance is achieved.

Summary of experimental results: The performance of the catalyst systems for each of the comparative and inventive systems are summarized below. The results are tabulated under Table 5:

TABLE 5

Summary of reactor system performance

| Experiment Code | High Selectivity Catalyst Component | Low Selectivity Catalyst Component | Ignition Temperature (° C.) | Maximum $C_{2+}$ hydrocarbon selectivity (%) | CE Carbon Efficiency (%) |
|---|---|---|---|---|---|
| Comparative Ex 1 (CE1) | CE 1 (100%) | NA | 700 | 77.5 | 75.8 |
| Comparative Ex 2 (CE2) | NA | CE 2 (100%) | 550 | 38.9 | NA |
| Inventive Experiment 1 (EX1) | CE 1 (85%) | CE 2 (15%) | 550 | 74.1 | 74.3 |
| Comparative Ex 3 (CE3) | NA | CE 3 (100%) | 550 | 20.7 | NA |
| Inventive Experiment 2 (EX2) | CE 1 (85%) | CE 3 (15%) | 550 | 72.5 | 73.2 |
| Comparative Ex 4 (CE4) | NA | CE 4 (100%) | 550 | 15.3 | NA |
| Inventive Experiment 3 (EX3) | CE 1 (85%) | CE 4 (15%) | 550 | 72.6 | 73.6 |
| Comparative Ex 5 (CE5) | CE 1 (90%) | CE 2 (10%) | 700 | 77.2 | NA |

As shown in Table 5, it is evident that the inventive reactor systems demonstrate a balance of low ignition temperature and high selectivity for $C_{2+}$ hydrocarbons. As a result reactor systems containing the catalysts systems of EX1, EX2 and EX3 are particularly suitable to manage both catalyst bed temperature as well as obtain high $C_{2+}$ hydrocarbon selectivity. From the results shown under comparative example CE5 it is evident that only when the catalyst bed is loaded with the low selectivity catalyst component in an amount great than 10 wt. %, the desired balance of ignition temperature and catalyst selectivity is obtained. Thus the present invention demonstrates that only when a reactor system is configured with a specific combination of catalyst components as described in this disclosure that the unique combination of high catalyst selectivity and low ignition temperature is obtained.

The invention claimed is:

1. A reactor system for oxidative coupling of methane (OCM), comprising:
   a) an inlet configured to receive a reactant mixture;
   b) a reaction chamber having an upstream end and a downstream end such that the reaction chamber extends from the upstream end to the downstream end, wherein the reaction chamber comprises a catalyst bed having a catalyst composition having at least two catalyst components:
      i. a low selectivity catalyst component;
      ii. a high selectivity catalyst component;
   c) an outlet configured to recover a $C_{2+}$ hydrocarbon product mixture from the reactor system;

wherein the reactor system is configured such that the reactant mixture substantially contacts the high selectivity catalyst component prior to contacting the low selectivity catalyst component and wherein (a) the high selectivity catalyst component is represented by a general formula (I): $(AE_aRE1_bRE2_cAT_dO_x)/M_mO_n$, and (b) the low selectivity catalyst component is represented by a general formula (II): $(AM)_z\text{-}(AE_aRE1_bRE2_cAT_dO_x)/M_mO_n$; wherein, (i) 'AE' represents an alkaline earth metal; (ii) 'RE1' represents a first rare earth element; (iii) 'RE2' represents a second rare earth element; (iv) 'AT' represents a third rare earth element 'RE3', or a redox agent 'RX' selected from antimony, tin, nickel, chromium, molybdenum, tungsten, manganese, bismuth; wherein, 'a', 'c', and 'd' each independently represent relative molar ratio; wherein 'a' ranges from 0.1 to 5; 'b' ranges from 0.1 to 10; 'c' ranges from 0.01 to about 10; 'd' ranges from 0.01 to 10;'x' balances the oxidation state; wherein, the first rare earth element, the second rare earth element and the third rare earth element, are different; (v) 'AM' represents a metal promoter selected from Group 4 to Group 12 of the Periodic Group of Elements; (vi) 'z' represents the amount of metal promoter present in the low selectivity catalyst component and 'z' ranges from 0.01 wt. % to 1.0 wt. % with regard to the weight of the low selectivity catalyst component; and (vii) '$M_mO_n$' represents an oxide catalyst support, wherein 'M' is selected from a metal or silicon; 'm' and 'n' are any positive integers and ranges from about 1 to about 5.

2. The reactor system according to claim 1, wherein the catalyst bed comprises the low selectivity catalyst component present in an amount greater than 10 wt. %, with regard to the total weight of the catalyst composition.

3. The reactor system according to claim 1, wherein the high selectivity catalyst component is positioned proximal to the inlet and the low selectivity catalyst component is positioned proximal to the outlet.

4. The reactor system according to claim 1, wherein the high selectivity catalyst component is positioned at the upstream end of the reactor chamber and the low selectivity catalyst component is positioned at the downstream end of the reactor chamber.

5. The reactor system according to claim 1, wherein the catalyst bed comprises the high selectivity catalyst component present in an amount of at least 50 wt. % to less than 90 wt. % with regard to the total weight of the catalyst composition.

6. The reactor system according to claim 1, wherein the high selectivity catalyst component and the low selectivity catalyst component are in contact with each other.

7. The reactor system according to claim 1, wherein the low selectivity catalyst component is characterized by an ignition temperature of at least 100° C. lower than the ignition temperature of the high selectivity catalyst component, when each of the low selectivity catalyst component and the high selectivity catalyst component is subjected to a reaction condition sufficient to produce $C_{2+}$ hydrocarbon mixture product.

8. The reactor system according to claim 1, wherein the catalyst composition is characterized by a $C_{2+}$ hydrocarbon product selectivity of greater than 70% with regard to the total product formed and an ignition temperature of less than 700° C. when the catalyst composition is subjected to a reaction condition sufficient to produce $C_{2+}$ hydrocarbon mixture product, and/or wherein the ratio of $C_{2+}$ hydrocarbon product selectivity of the high selectivity catalyst component to the $C_{2+}$ hydrocarbon product selectivity of the low selectivity catalyst component is greater than 1.5.

9. The reactor system according to claim 8, wherein the metal promoter 'AM' is selected from the Group 10 metals of the Periodic Group of Elements.

10. The reactor system according to claim 8, wherein the metal promoter 'AM' is present in an amount 'z' ranging from 0.01 wt. % to 0.1 wt. %, with regard to the weight of the low selectivity catalyst component.

11. The reactor system according to claim 8, wherein the alkaline earth metal 'AE' is selected from the group consisting of magnesium, calcium, strontium, barium, and combinations thereof.

12. The reactor system according to claim 8, wherein the first rare earth element 'RE1', the second rare earth element 'RE2', and the third rare element 'RE3', are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof.

13. The reactor system according to claim 8, wherein the oxide catalyst support $M_mO_n$ is selected from aluminum oxide ($Al_2O_3$), zinc oxide, tin (II) oxide, and lead (II) oxide.

14. A process for producing a $C_{2+}$ hydrocarbon mixture product, comprising:
(a) introducing the reactant mixture comprising methane and oxygen, into the reactor system according to claim 1 by means of the inlet;
(b) substantially contacting the reactant mixture with the high selectivity catalyst component and thereafter substantially contacting the reactant mixture with the low selectivity catalyst component to form a precursor hydrocarbon mixture product; and removing unconverted methane from the precursor hydrocarbon mixture product and thereafter recovering the $C_{2+}$ hydrocarbon mixture product by means of the outlet.

15. The reactor system according to claim 8, wherein the metal promoter 'AM' is palladium.

16. The reactor system according to claim 8, wherein the alkaline earth metal 'AE' is strontium.

17. The reactor system according to claim 8, wherein the oxide catalyst support $M_mO_n$ is aluminum oxide ($Al_2O_3$).

18. The reactor system according to claim 8, wherein the catalyst composition is characterized by a $C_2$-hydrocarbon product selectivity of greater than 70% with regard to the total product formed.

19. The reactor system according to claim 8, wherein the metal promoter 'AM' is present in an amount 'z' ranging from 0.02 wt. % to 0.08 wt. %, with regard to the weight of the low selectivity catalyst component.

20. The process according to claim 14, wherein the reactant mixture has a methane to oxygen molar ratio ranging from 4:1 to 10:1; and wherein the reactant mixture is preheated to a temperature of from 200° C. to 300° C. prior to introducing the reactant mixture into the reactor system.

* * * * *

UNITED STATES PATENT AND TRADEMARK OFFICE
CERTIFICATE OF CORRECTION

PATENT NO. : 11,969,724 B2
APPLICATION NO. : 18/038547
DATED : April 30, 2024
INVENTOR(S) : Wugeng Liang et al.

It is certified that error appears in the above-identified patent and that said Letters Patent is hereby corrected as shown below:

In the Specification

Column 16 Line 5 replace "85 wt. % omgmgf" with --85 wt. % of--

Signed and Sealed this
Eighteenth Day of June, 2024

Katherine Kelly Vidal
Director of the United States Patent and Trademark Office